United States Patent
Choi et al.

(10) Patent No.: US 10,595,728 B2
(45) Date of Patent: Mar. 24, 2020

(54) SYSTEMS AND METHODS FOR PREDICTING TISSUE VIABILITY DEFICITS FROM PHYSIOLOGICAL, ANATOMICAL, AND PATIENT CHARACTERISTICS

(71) Applicant: HeartFlow, Inc., Redwood City, CA (US)

(72) Inventors: Gilwoo Choi, Mountain View, CA (US); Michiel Schaap, Mountain View, CA (US); Charles A. Taylor, Menlo Park, CA (US); Leo Grady, Millbrae, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 15/088,969

(22) Filed: Apr. 1, 2016

(65) Prior Publication Data

US 2016/0287093 A1    Oct. 6, 2016

Related U.S. Application Data

(60) Provisional application No. 62/142,172, filed on Apr. 2, 2015.

(51) Int. Cl.
| | |
|---|---|
| *A61B 5/02* | (2006.01) |
| *G16H 50/30* | (2018.01) |
| *G16H 50/50* | (2018.01) |
| *G16H 50/20* | (2018.01) |
| *A61B 5/026* | (2006.01) |
| *A61B 5/00* | (2006.01) |

(52) U.S. Cl.
CPC .......... *A61B 5/02007* (2013.01); *A61B 5/026* (2013.01); *A61B 5/742* (2013.01); *G16H 50/20* (2018.01); *G16H 50/30* (2018.01); *G16H 50/50* (2018.01)

(58) Field of Classification Search
None
See application file for complete search history.

(56) References Cited

U.S. PATENT DOCUMENTS

| | | | | |
|---|---|---|---|---|
| 7,693,315 | B2 * | 4/2010 | Krishnan | G06T 7/0012 382/100 |
| 8,315,812 | B2 * | 11/2012 | Taylor | A61B 5/02007 382/128 |
| 2015/0038860 | A1 | 2/2015 | Fonte | |

OTHER PUBLICATIONS

Schinkel et al. (Journal of Nuclear Medicine (2007) vol. 48:1135-1146).*
O'Donnell et al. (International Journal of Computer Vision (2006) vol. 70:165-178).*
Wu et al., "Noninvasive Imaging of Myocardial Viability: Current Techniques and Future Developments," Circ. Res., 2003, vol. 93, pp. 1146-1158.
Mendoza, D. et al., "Evaluation of myocardial viability by multidetector CT," Journal of Cardiovascular Computed Tomography, 2009, vol. 3, Suppl. 1:, pp. S2-S12.

* cited by examiner

*Primary Examiner* — Lori A. Clow
(74) *Attorney, Agent, or Firm* — Bookoff McAndrews, PLLC

(57) ABSTRACT

Systems and methods are disclosed for using patient-specific anatomical models and physiological parameters to predict viability of a target tissue or vessel to guide diagnosis or treatment of cardiovascular disease. One method includes: receiving a patient-specific vessel model and a patient-specific tissue model of a patient anatomy; receiving one or more patient-specific physiological parameters (e.g. blood flow, anatomical characteristics, etc.) for one or more physiological states; estimating a viability characteristic of the patient-specific tissue or vessel model (e.g., via a trained machine learning algorithm), using the patient-specific physiological parameters; and outputting the viability characteristic to an electronic storage medium or display.

20 Claims, 5 Drawing Sheets

SYSTEMS AND METHODS FOR PREDICTING TISSUE VIABILITY DEFICITS FROM PHYSIOLOGICAL, ANATOMICAL, AND PATIENT CHARACTERISTICS

RELATED APPLICATIONS

This application claims priority under 35 U.S.C. § 119(e) to U.S. Provisional Application No. 62/142,172, filed Apr. 2, 2015, the contents of which are hereby incorporated herein by reference in their entirety.

FIELD OF DISCLOSURE

Various embodiments of the present disclosure relate generally to disease assessment, treatment planning, and related methods. More specifically, particular embodiments of the present disclosure relate to systems and methods for assessing and treating ischemia.

BACKGROUND

Ischemia is a common ailment that affects millions of people. Ischemia is a restriction in the blood supply to biological tissues causing a shortage of oxygen and glucose needed for cellular metabolism. As a result, damage or dysfunction may result in the tissues, and a local anemia may develop in parts of the body resulting from congestion. A patient suffering from ischemia may experience irreversible damage to bodily tissues in as little as 20 minutes. A more severe manifestation of disease may lead to tissue necrosis and/or gangrene. Significant strides have been made in the measurement of ischemia including using specialized imaging techniques (e.g., Contrast-Enhanced Magnetic Resonance Imaging (CEMRI), Fludeoxyglucose Positiron Emission Tomography (FDG-PET), stress echo/MRI, multidetector CT, and/or dual energy CT). However, these imaging techniques may incur a significant financial expense and may also expose a patient to additional radiation. Furthermore, the equipment required to perform the specialized imaging techniques may not be available at some facilities. Since viability is the degree to which a vessel, tissue, or organ is functional, an ischemia may result in reduced viability of the underlying vessel, tissue, or organ. Thus, a desire exists to use available patient information to estimate a viability characteristic in a target tissue, where the estimated viability data may be obtained by machine learning from a patient-specific vascular and/or anatomical model, and by using any other additional data that may be available. Since the vascular and/or anatomical model may be derived from several imaging techniques, the embodiments of the present disclosure may enable use of a single scan to assess both tissue anatomy and tissue viability.

The foregoing general description and the following detailed description are exemplary and explanatory only and are not restrictive of the disclosure.

SUMMARY

According to certain aspects of the present disclosure, systems and methods are disclosed for using available patient information to estimate viability of a target tissue or vessel to guide diagnosis or treatment of cardiovascular disease.

One method includes: receiving a patient-specific vessel model or tissue model of a patient anatomy; receiving one or more patient-specific physiological parameters for one or more physiological states; estimating a characteristic of tissue viability of the patient-specific vessel model or target tissue model, using the patient-specific physiological parameters; and outputting the estimated characteristic of tissue viability to an electronic storage medium or display.

In accordance with another embodiment, a system for estimating patient-specific tissue viability, the system comprising: a data storage device storing instructions for determining characteristics of tissue viability; and a processor configured to execute the instructions to perform a method including the steps of: receiving a patient-specific vessel model or tissue model of a patient anatomy; receiving one or more patient-specific physiological parameters for one or more physiological states; estimating a characteristic of tissue viability of the patient-specific vessel model or target tissue model, using the patient-specific physiological parameters; and outputting the estimated characteristic of tissue viability to an electronic storage medium or display.

In accordance with another embodiment, a non-transitory computer readable medium for use on a computer system containing computer-executable programming instructions for estimating a characteristic of tissue viability, the method comprising: receiving a patient-specific vessel model or tissue model of a patient anatomy; receiving one or more patient-specific physiological parameters for one or more physiological states; estimating a characteristic of tissue viability of the patient-specific vessel model or target tissue model, using the patient-specific physiological parameters; and outputting the estimated characteristic of tissue viability to an electronic storage medium or display.

Additional objects and advantages of the disclosed embodiments will be set forth in part in the description that follows, and in part will be apparent from the description, or may be learned by practice of the disclosed embodiments. The objects and advantages on the disclosed embodiments will be realized and attained by means of the elements and combinations particularly pointed out in the appended claims.

It is to be understood that both the foregoing general description and the following detailed description are exemplary and explanatory only and are not restrictive of the detailed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

FIG. 4 may also disclose a method of performing steps 208 or 322 in FIG. 2 and FIG. 3, respectively, which is determining an estimate of tissue viability.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Ischemia is a common ailment, by which blood flow to the bodily tissues may be restricted. While significant strides have been made in the treatment of ischemia, the treatment is often misplaced or excessive. For example, patients often undergo scans which may be costly and/or expose the patient to unnecessary radiation. Patients are sometimes subjected to treatments that may not change their condition. In some situations, patients even undergo treatments that ultimately worsen their condition. Thus, a need exists to accurately assess the severity of ischemia and/or predicting ischemia to aid in selecting a course of treatment. For the purposes of the disclosure: "patient" may refer to any individual or person for whom diagnosis or treatment of ischemia is performed or characteristics of tissue viability are being estimated, or any individual or person associated with the diagnosis, treatment, or tissue viability analysis of one or more individuals.

Since viability is the degree to which a vessel, tissue, or organ is functional, an ischemia may result in reduced viability of the underlying vessel, tissue, or organ. The embodiments of the present disclosure may provide systems and methods of using available patient information to estimate a viability characteristic in a target tissue, where the estimated viability data may be obtained by machine learning from a patient-specific vascular and/or anatomical model, and/or by using any other additional data that may be available. A "target tissue" may refer to a tissue and/or organ in which the blood supply and/or viability characteristics may be estimated. Since the vascular and/or anatomical model may be derived from several imaging techniques, the embodiments of the present disclosure may enable use of a single scan to assess both tissue anatomy and tissue viability.

Figure 1:
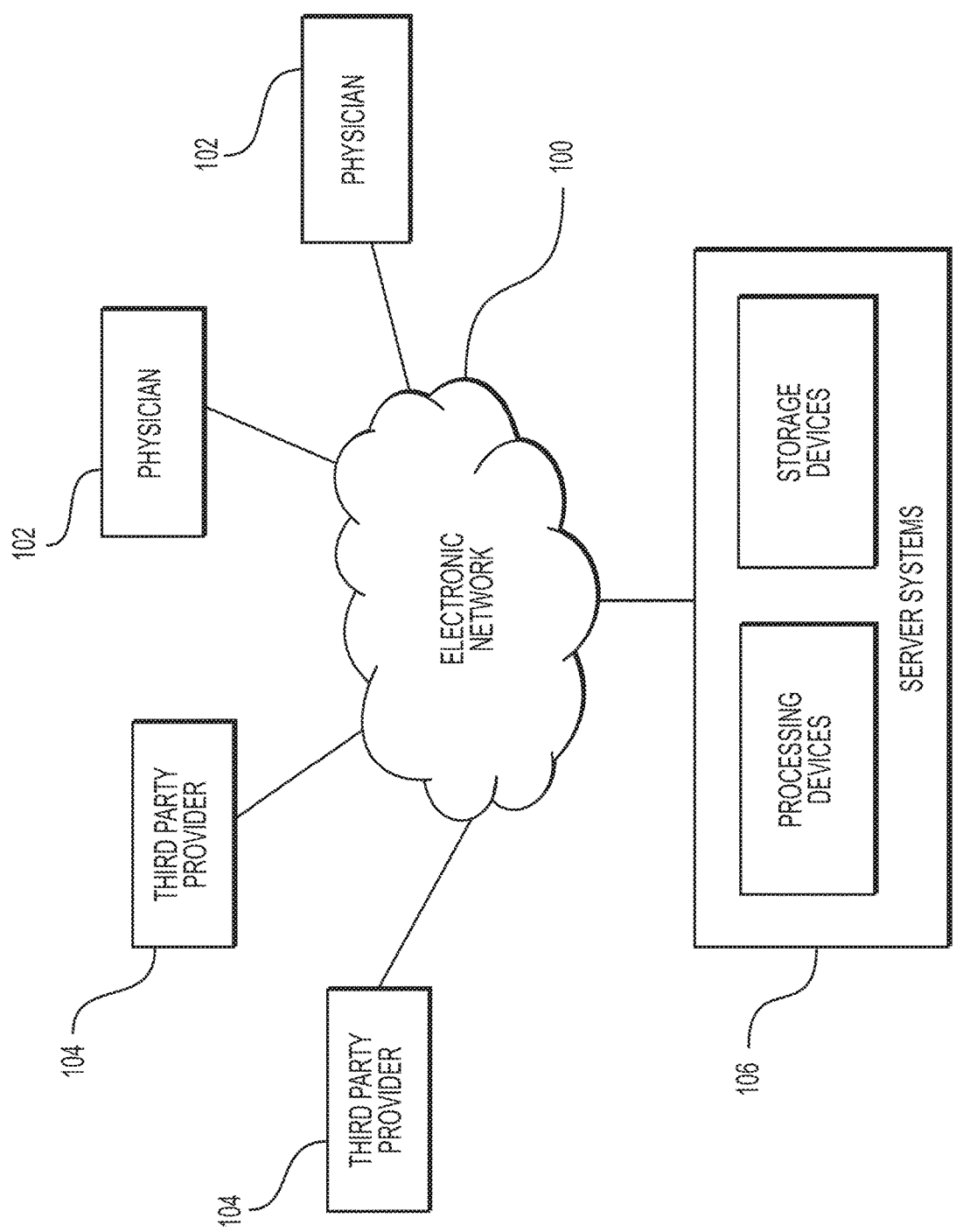
FIG. 1 is a block diagram of an exemplary system and network for predicting tissue viability to guide diagnosis or treatment of ischemia, according to an exemplary embodiment of the present disclosure.

Referring now to the figures, FIG. 1 depicts a block diagram of an exemplary system 100 and network for estimating tissue viability to guide diagnosis or treatment of cardiovascular disease, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

Figure 2:
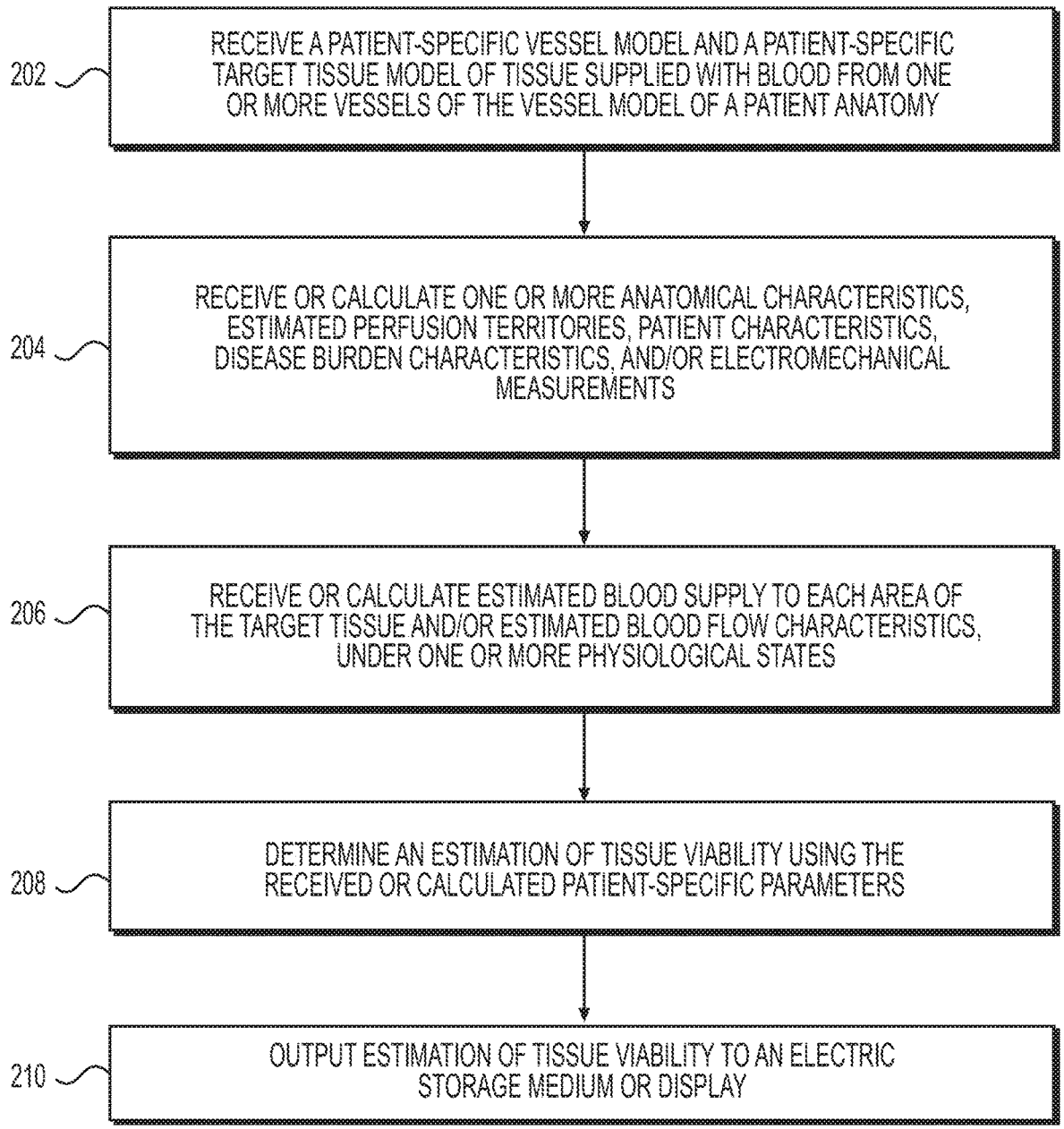
FIG. 2 is a block diagram of a general method of estimating tissue viability, according to a general embodiment of the present disclosure.

FIG. 2 depicts a general embodiment of an exemplary method 200 for estimating tissue viability to guide diagnosis or treatment of ischemia. The method of FIG. 2 may be performed by server systems 106, based on information, images, and data received from physicians 102 and/or third party providers 104 over electronic network 101.

In one embodiment, step 202 may include receiving a patient-specific vessel model and a patient-specific target tissue model of tissue supplied with blood from the vessels of the vessel model of a patient anatomy in an electronic storage medium of the storage system 106. An "electronic storage medium" may include, but is not limited to, a hard drive, network drive, cloud drive, mobile phone, tablet, or the like that may or may not be affixed to a display screen. Specifically, receiving the patient-specific vessel model and/or patient-specific target tissue model may include either generating the patient-specific anatomical model at the server system 106, or receiving one over an electronic network (e.g., electronic network 101). The patient-specific vessel model and patient-specific target tissue model may include a cardiovascular model or any other anatomical model of a biological tissue or system of a specific person. In one embodiment, the vessel model and target tissue model may be derived from images of the person acquired via one or more available imaging or scanning modalities (e.g., computed tomography (CT) scans and/or magnetic resonance (MR) imaging). For example, step 202 may include receiving CT and/or MR images of a person's heart. Step 202 may further include generating, from the received images, a patient-specific vessel model and target tissue model for the particular person.

In one embodiment, step 204 and 206 may include receiving or calculating one or more patient-specific physiological parameters. These patient-specific physiological parameters may be received or calculated from the received vessel model, the received target tissue model, one or more medical images of the patient, and/or medical records of the patient. These patient-specific physiological parameters may include anatomical characteristics, as well as secondary characteristics related to the patient and/or the patient's anatomy (e.g., patient characteristics, disease burden characteristics, and electromechanical measurements). The patient-specific physiological parameters may also include parameters related to blood circulation, including an estimation of the blood supply to each area of a target tissue and/or blood flow characteristics, under one or more physiological states.

One instance of a physiological state may be a resting state. Another physiological state may be a physiological state other than the resting state, or an "active" physiological state. Active physiological states may include hyperemia, various levels of exercise, post prandial, positional (e.g., supine-upright), gravitational (e.g. G-forces, zero gravity, etc.), or a combination thereof. In one embodiment, steps and/or 206 may further include determining, specifying, and/or selecting one or more physiological states by comparing physiological parameters at a physiological state different from a patient resting state. In one embodiment, the patient-specific physiological parameters may be obtained from sources other than the vessel model and/or target tissue model.

Specifically, step 204 may include receiving or calculating one or more anatomical characteristics, patient characteristics, disease burden characteristics, and/or electromechanical characteristics, under one or more physiological states. Step 204 may further include receiving or calculating one or more image characteristics, e.g., derived from locations of the patient-specific vessel model or locations of the patient-specific target tissue model. For example, image characteristics may be determined from renderings of regions, points, or sections of the patient-specific vessel model or the patient-specific target tissue model.

In one embodiment, step 206 may include receiving or calculating an estimated supplied blood to each area of a target tissue or to each vessel in a vascular network and/or estimated blood flow characteristics, under one or more physiological states. These estimations may be based on a measurement (e.g., by measuring through imaging) or via an estimation of supplied blood in a resting state (e.g., based on a 3D simulation, a 1D simulation, or a learned relationship).

In one embodiment, step 208 may include determining an estimation of viability in one or more vessels and/or areas of a target tissue, using joint prior information. The joint prior information may refer to the one or more physiological parameters determined from steps 204 and 206. In one embodiment, determining an estimation of viability may involve determining an estimation of supplied blood at one or more vessel locations of the person's vessel model, while the person is in one or more physiological states, in order to determine viability of a tissue and/or vessel. The determination of tissue and/or vessel viability may also be based on a measurement of blood flow characteristics (e.g., by imaging) or via an estimation of blood flow characteristics in one or more physiological states (e.g., based on a 3D simulation, a 1D simulation, or a learned relationship). In one embodiment, determining tissue viability may include an estimation of the perfusion territories of the target tissue related to the vascular model. The estimation of perfusion territories may be determined by using a nearest-neighbor (e.g., Voronoi diagram) approach to assign locations in the target tissue to the closest supplying vessel in the vascular model. The estimation of perfusion territories may also be determined using a microvascular estimation technique from an anatomical model, for example, by using a constrained constructive optimization approach. In one embodiment, step 208 may include estimating viability at one or more locations of the target tissue and/or vessel in one or more physiological states using a trained machine learning algorithm. Step 208 may be performed by a processor.

In one embodiment, step 210 may include outputting the estimation of viability of the tissue and/or vessel to an electronic storage medium (e.g., hard disk, network drive, portable disk, smart phone, tablet etc.) and/or to a display screen. In one embodiment, the output viability estimates may be displayed in greyscale or color in 2D or 3D. The calculated tissue and/or vessel viability estimates may be overlaid on the anatomical model of the target tissue and/or overlaid on an image of the target tissue. In one embodiment, step 210 may include estimating tissue viability designed to simulated a SPECT or PET scan in one or more physiological states. In one embodiment, the estimation may be performed by modeling contrast agent in the concentrations given by the viability estimates. In another embodiment, the estimation may involve performing a Monte Carlo simulation to estimate the collimation of photons or positrons at virtual collimator locations. Using the collimator estimation, a SPECT or PET image may be reconstructed using standard tomographic techniques. The estimated tissue viability characteristics may be saved to an electronic storage medium and/or displayed on a monitor.

Figure 3:
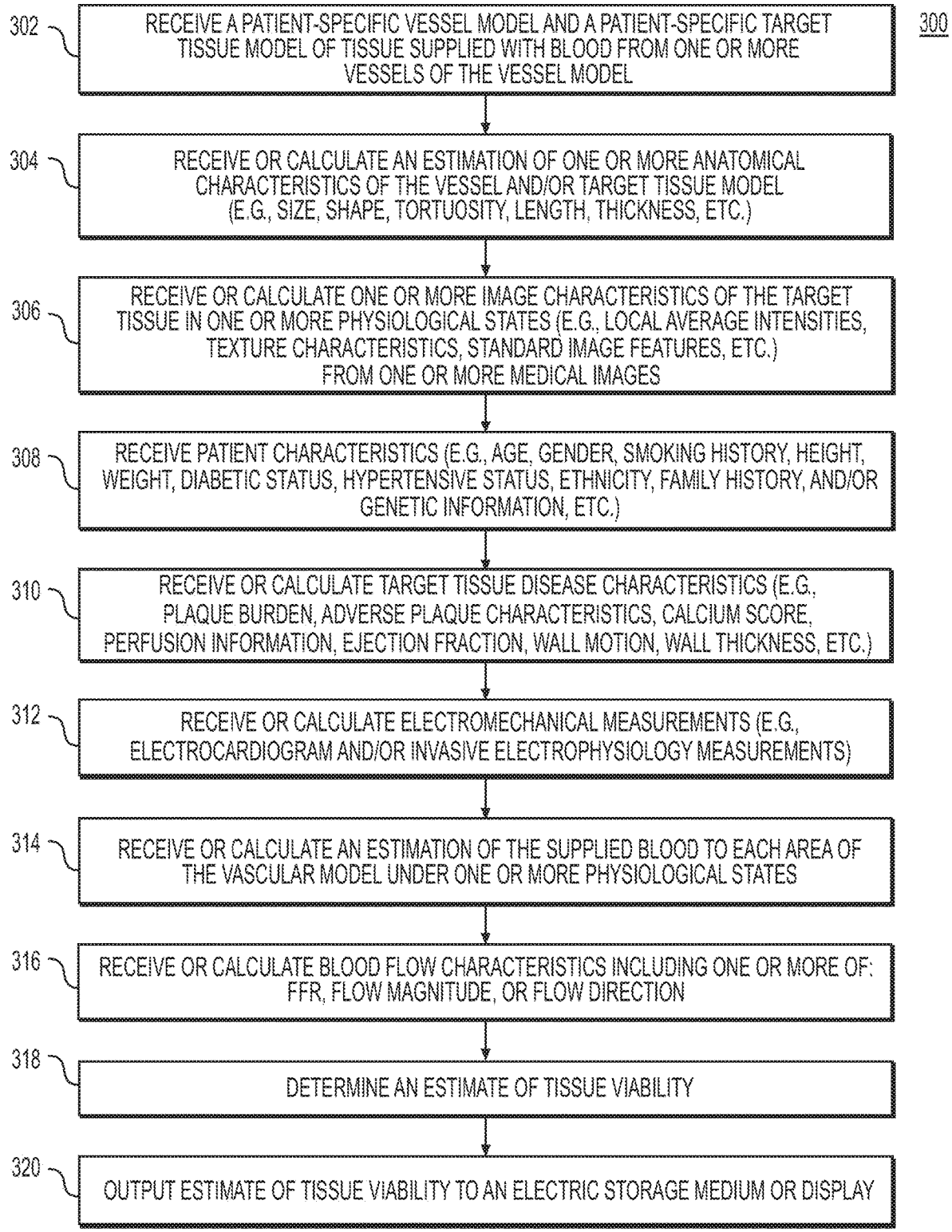
FIG. 3 is a block diagram of an exemplary method of estimating tissue viability, according to an exemplary embodiment of the present disclosure.

FIG. 3 depicts an exemplary embodiment of method 300 for estimating tissue viability to guide diagnosis or treatment of ischemia. The method of FIG. 3 may be performed by server systems 106, based on information, images, and data received from physicians 102 and/or third party providers 104 over electronic network 101.

In one embodiment, step 302 may include receiving a patient-specific vessel model or target tissue model of a patient anatomy in an electronic storage medium of the storage system 106. Specifically, receiving the patient-specific vessel model or target tissue model may include either generating the patient-specific vessel model or target tissue model at the server system 106, or receiving the patient-specific vessel model or target tissue model over an electronic network (e.g., electronic network 101). In one embodiment, the vessel model or target tissue model may be derived from images of the person acquired via one or more available imaging or scanning modalities (e.g., CT scans and/or magnetic resonance imaging). For example, step 302 may include receiving CT and/or MRI images of a person's heart. Step 302 may further include generating, from the received images, a patient-specific cardiovascular model, a model of any biological system for the particular person, or a target tissue of the particular person.

In one embodiment, step 304 may include receiving or calculating an estimation of one or more of the anatomical characteristics of the target tissue. The anatomical characteristics may include, but are not limited to, vessel size, vessel shape, tortuosity, thickness, and the like. This calculation may be based on a measurement (e.g., by measuring the anatomical characteristics from imaging) or via an estimation of the anatomical characteristics in a resting state (e.g., based on a 3D simulation, a 1D simulation, or a learned relationship).

In one embodiment, step 306 may include receiving or calculating one or more image characteristics of the target tissue of the vascular model from one or more medical images of the patient. The medical images may be in the form of CT scan images, MRI images, ultrasound images, PET images, or SPECT images. The images may capture the vascular model in one or more physiological states (e.g., rest, stress, active). The image characteristics of the target tissue or vessels may be received or calculated for one or more locations of the vascular system or target tissue. The image characteristics may include, but are not limited to, local average intensities at one or more image resolutions, differences of the average intensities (e.g., calculated via wavelet bases, using for example, Haar wavelets), texture characteristics (e.g., Haralick texture features), any standard image features including histograms of gradients, SIFT, steerable filters, and characteristics related to an imaging or scanning modality, etc.

In one embodiment, step 308 may include receiving patient characteristics. The patient characteristics may include, but are not limited to, age, gender, smoking history, height, weight, diabetic status, hypertensive status, ethnicity, family history, blood type, prior history of drug use, and/or genetic history. The patient characteristics may be obtained via the electronic network 100 or from the patient's physician 102 or from a third party provider 103.

In one embodiment, step 310 may include receiving or calculating disease burden characteristics of the target tissue and/or vessels. The disease burden characteristics may include, but are not limited to, the presence and extent of plaque buildup within the arteries, the presence of plaque characteristics (e.g., spotty calcification, low attenuation plaque, napkin-ring sign, positive remodeling), patient level or vessel level calcium scores, tissue viability information, vessel wall motion, vessel wall thickness, and/or ejection fraction.

In one embodiment, step 312 may include, receiving or calculating electromechanical measurements. The electromechanical measurements may include, but are not limited to, electrocardiography (ECG) measurements, or invasive electrophysiology (EP) measurements.

In one embodiment, step 314 may include receiving or calculating an estimation of the supplied blood to each area of the target tissue under one or more physiological states. One instance of a physiological state may be a resting state. This calculation may be based on a measurement (e.g., by measuring by imaging) or via an estimation of supplied blood in a resting state (e.g., based on a three-dimensional (3D) simulation, a one-dimensional (1D) simulation, or a learned relationship). Another physiological state may be a physiological state other than the resting state, or an "active" physiological state. One instance of such a physiological state may include hyperemia. Other non-resting physiological states may include, various levels of exercise, post prandial, positional (e.g., supine-upright), gravitational (e.g. G-forces, zero gravity, etc.).

In one embodiment, step 316 may include receiving or calculating one or more blood flow characteristics of the target tissue. In one embodiment, the blood flow characteristic may include, but is not limited to, a fractional flow reserve value (FFR), flow direction and/or flow magnitude, and may be determined by an estimation of blood flow to the target tissue. In one embodiment, the blood flow characteristic may be calculated by several means, including, but not limited to, invasive measurements (e.g., invasive FFR, thrombosis in myocardial infarction (TIMI), or microspheres), calculation using a blood flow simulation model (e.g., a 3D or 1D fluid simulation model, calculation, or TAFE), calculation using image characteristics (e.g., TAG or CCO) derived from one or more medical images, or calculation using a machine learning estimation of blood supply based on anatomical or imaging features. In one embodiment, step 316 may include calculating an estimation of the blood flow in the perfusion territories of the target tissue related to the vessel model. This estimation may be determined by using a nearest-neighbor (e.g., Voronoi diagram) approach to assigning locations in the target tissue to the closest supplying blood vessel in the vascular model. The estimation may also be determined using a microvascular estimation technique from an anatomical model, for example, by using a constrained constructive optimization approach. In one embodiment, step 316 may be performed by a processor. The processor may estimate tissue viability at one or more locations of the target tissue in the vascular model in one or more psychological states by machine learning.

In one embodiment, step 318 may include determining an estimate of one or more tissue viability characteristics at one or more locations in the target tissue related to the vascular model. The estimation of tissue viability characteristics may be calculated for one or more physiological states using the one or more physiological parameters (e.g., anatomical characteristics, estimated blood supply, estimated blood flow characteristics, estimated perfusion territories, patient characteristics, disease burden characteristics, and/or electromechanical measurements) and/or image characteristics from one or more medical images. In one embodiment, this calculation of tissue viability may be performed by training a machine learning algorithm using a database of patients with known tissue viability characteristics and known patient-specific physiological parameters, including, but not limited to, the anatomical characteristics, estimated perfusion territories, disease burden characteristics, and/or electromechanical measurements. In one embodiment step 318 may be performed using a processor.

In one embodiment, step 320 may include outputting the estimation of tissue viability to an electronic storage medium (e.g., hard disk, network drive, portable disk, smart phone, tablet, etc.) and/or to a display screen. In one embodiment, the output tissue viability estimates may be displayed in greyscale or color in 2D or 3D. In one embodiment, the output tissue viability estimates may be overlaid or superimposed on the anatomical model of the target tissue and/or overlaid or superimposed on an image of the target tissue. In one embodiment, this determination may be performed by training a machine learning algorithm using a database of patients with known tissue viability characteristics and known patient-specific physiological parameters.

The above recited steps of methods 200 and 300 may be used to estimate tissue viability in a variety of biological tissues, including, but not limited to, the myocardium using a coronary vascular model, the brain using a cerebral vascular model, muscle tissue using a peripheral vascular model, the liver using a hepatic vascular model, the kidney using a renal vascular model, the bowel using a visceral vascular model, and in other organs including the spleen and pancreas, using a vascular model for vessels supplying blood to the target organ.

In one embodiment, the tissue viability estimation may also be used to enhance a blood flow simulation by using more accurate boundary conditions to perform a simulation or estimation of blood flow characteristics.

In one embodiment, treatment planning and diagnosis may be improved by virtually changing the input information (e.g. the vascular model, tissue model, patient-specific physiological parameters, etc.). Such changes may include virtual revascularization of the vascular model, modifying the tissue model, patient characteristics, etc.). Yet another embodiment may include predicting the effects on tissue viability in the target tissue based on the changed inputs (e.g., predicting the functional recovery of the target tissue in response to a changed input using the estimated viability information).

Figure 4:
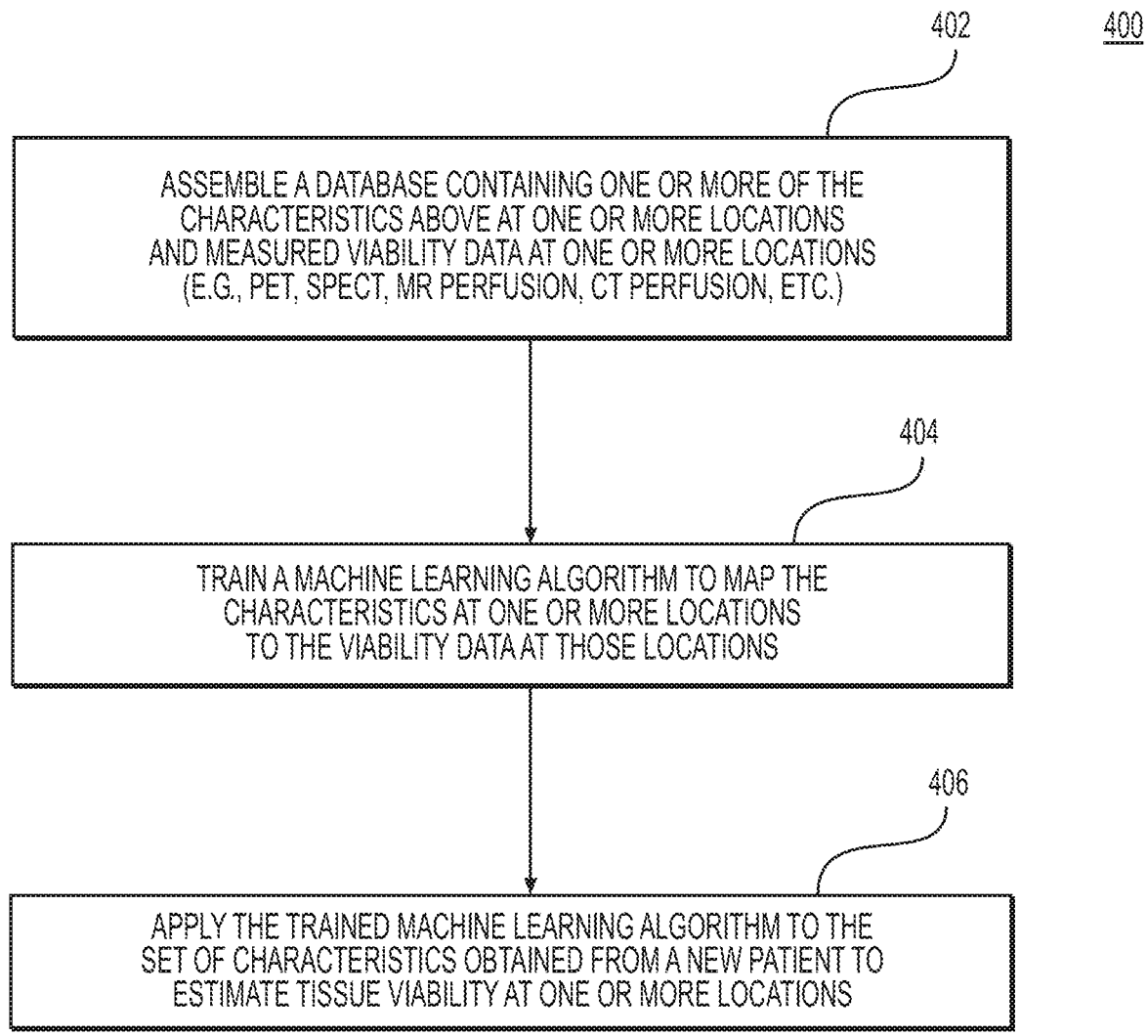
FIG. 4 is a block diagram of an exemplary method of estimating tissue viability using machine learning, according to an exemplary embodiment of the present disclosure.

FIG. 4 depicts an exemplary embodiment of method 400 for training a machine learning algorithm to determine an estimate of tissue viability at one or more locations in the target tissue in one or more physiological states. The method of FIG. 4 may be performed by server systems 106, based on information, images, and data received from physicians 102 and/or third party providers 104 over electronic network 101.

In one embodiment, step 402 may include assembling a database containing one or more known physiological parameters from a plurality of patients at one or more locations of a vascular and/or target tissue model and the estimated or measured tissue viability at those locations. For the purpose of disclosure, "physiological parameters" may refer to one or more of the received or calculated anatomical characteristics, perfusion territories, blood supply to the target tissue, blood flow characteristics, patient characteristics, disease burden characteristics, and/or electromechanical measurements. The models may be obtained from one or more available imaging or scanning modalities, including, but not limited to, PET, SPECT, MR, CT, and/or a combination of these modalities. In one embodiment, the database may also include image characteristics derived from one or more medical images.

In one embodiment, step 404 may include training a machine learning algorithm to map the one or more physiological parameters at one or more locations of the vascular and/or target tissue model to the one or more characteristics of tissue viability those locations. The machine learning algorithm may take many forms, including, but not limited to, a multi-layer perceptron, deep learning, support vector machines, random forests, k-nearest neighbors, Bayes networks, etc. In one embodiment, image characteristics derived from one or more medical images may also be mapped along with the one or more physiological parameters, at one or more locations of the vascular and/or target tissue model, to the one or more characteristics of tissue viability those locations.

In one embodiment, step 406 may include applying the trained machine learning algorithm to the set of patient-specific physiological parameters of the vascular model and/or target tissue obtained from a new patient to estimate the tissue viability at one or more locations. In another embodiment, step 406 may include applying the trained machine learning algorithm to a set that includes patient-specific physiological parameters of the vascular model and/or target tissue obtained from a new patient and image characteristics derived from one or more medical images of the new patient, to estimate the tissue viability at one or more locations.

Figure 5:
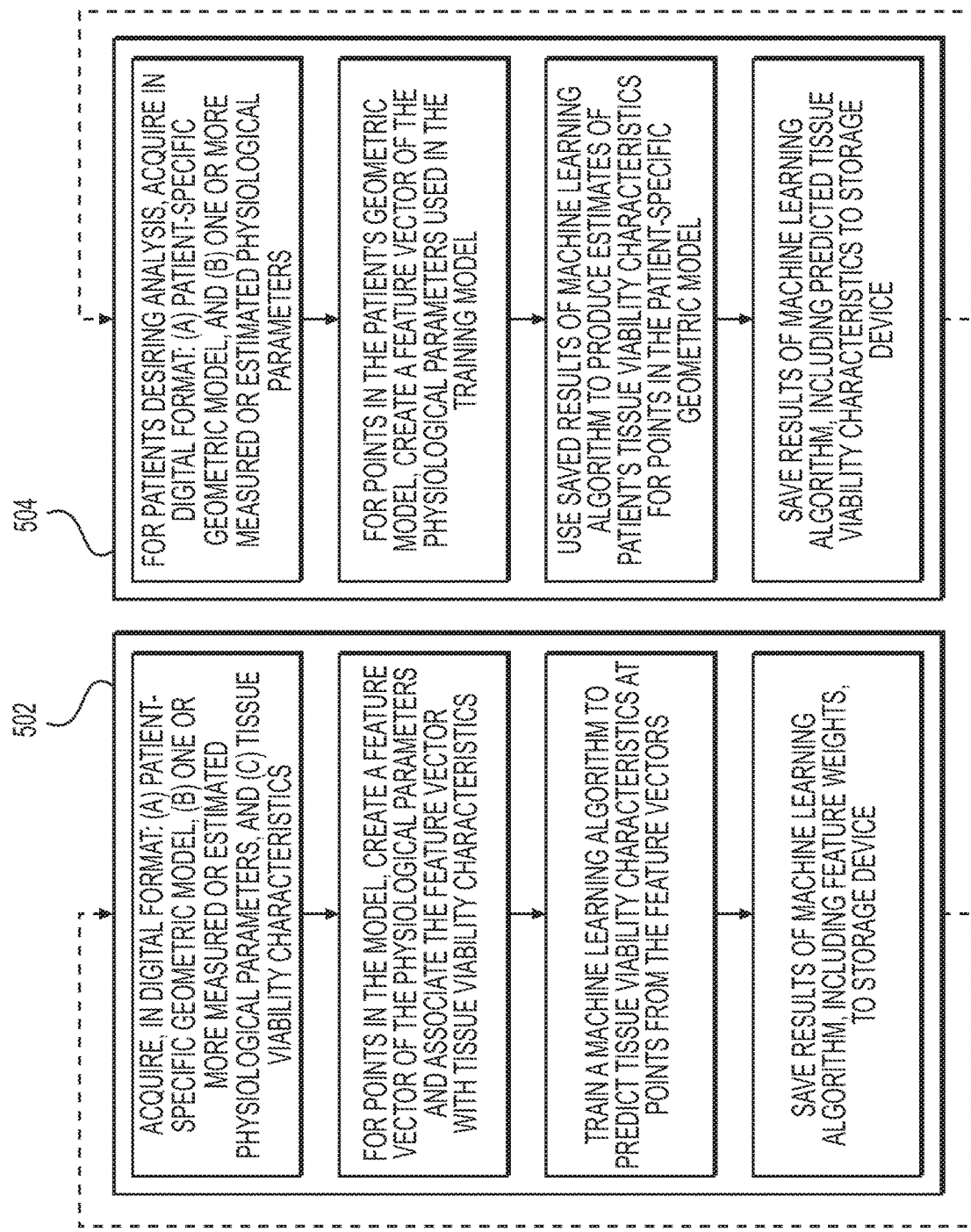
FIG. 5 is a block diagram examining the method disclosed in FIG. 4 in more detail. Furthermore, FIG. 5 discloses an exemplary method for estimating patient-specific viability characteristics from vessel geometry and physiological information, using machine learning, according to an exemplary embodiment of the present disclosure.

FIG. 5 is a block diagram of an exemplary method for estimating patient-specific tissue viability from vessel geometry and physiological information, according to an exemplary embodiment of the present disclosure. The method of FIG. 5 may be performed by server systems 106, based on information received from physicians 102 and/or third party providers 104 over electronic network 100.

In one embodiment, the method of FIG. 5 may include a training method 502, for training one or more machine learning algorithms based on numerous patients' physiological parameters and tissue viability estimates, and a production method 504 for using the machine learning algorithm results to predict a particular patient's tissue viability characteristics.

In one embodiment, training method 502 may involve acquiring, for each of a plurality of individuals, e.g., in digital format: (a) a patient-specific geometric model, (b) one or more measured or estimated physiological parameters, and (c) tissue viability characteristics. Training method 502 may then involve, for one or more points in each patient's model, creating a feature vector of the patients' physiological parameters and associating the feature vector with tissue viability characteristics. Image characteristics from one or more medical images, for each of a plurality of individuals, may also be included with the one or more measured or estimated physiological parameters for the purpose of creating the feature vector. Training method 502 may then train a machine learning algorithm (e.g., using processing devices of server systems 106) to predict tissue viability at each point of a geometric model, based on the feature vectors and estimated tissue viability. Training method 502 may then save the results of the machine learning algorithm, including feature weights, in a storage device of server systems 106. The stored feature weights may define the extent to which patient-specific physiological parameters or anatomical geometry are predictive of tissue viability characteristics. In another embodiment, training method 502 may be performed based on FFR estimates generated using computational fluid dynamics (CFD) techniques for a plurality of patients. Training method 502 may then involve associating an estimated FFR with every point in a patient's geometric model, and then creating a feature vector of the patients' physiological parameters and associating the feature vector with FFR estimates. Image characteristics from one or more medical images, for each of a plurality of individuals, may also be included with the one or more measured or estimated physiological parameters for the purpose of creating the feature vector. Training method 502 may then train a machine learning algorithm (e.g., using processing devices of server systems 106) to predict tissue viability at each point of a geometric model, based on the feature vectors and estimated FFR.

The production method 504 may involve estimating tissue viability characteristics for a particular patient, based on results of executing training method 502. In one embodiment, production method 504 may include acquiring, e.g. in digital format: (a) a patient-specific geometric model, and (b) one or more measured or estimated physiological parameters. For multiple points in the patient's geometric model, production method 504 may involve creating a feature vector of the physiological parameters used in the training mode. In one embodiment, image characteristics derived from one or more medical images of the particular patient may also be included with the one or more measured or estimated physiological parameters for the purpose of creating the feature vector. Production method 504 may then use saved results of the machine learning algorithm to produce estimates of the patient's blood flow and/or tissue viability characteristics for each point in the patient-specific geometric model. Finally, production method 504 may include saving the results of the machine learning algorithm, including predicted blood flow and/or tissue viability characteristics, to a storage device of server systems 106.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for estimating tissue viability of a patient's tissue, the method comprising:
   receiving tissue viability data for a plurality of individuals;
   receiving data of one or more physiological or anatomical parameters, for each of the plurality of individuals;
   training, by using a training set comprising the tissue viability data and the data of one or more physiological or anatomical parameters, a machine learning algorithm, wherein the machine learning algorithm maps the one or more physiological or anatomical parameters to tissue viability;
   receiving image data derived from one or more images of a patient's anatomy;
   generating one or more patient-specific models, each being a model of a vessel or tissue of the patient, using the image data;
   calculating patient-specific values of the one or more physiological or anatomical parameters based on the one or more patient-specific models;
   computing a tissue viability value by inputting the patient-specific values of the one or more physiological or anatomical parameters into the trained machine learning algorithm, wherein the trained machine learning algorithm includes feature weights defining an extent to which the one or more physiological or anatomical parameters are predictive of tissue viability; and
   outputting, to an electronic storage medium or a display, the computed tissue viability value or a treatment plan generated based on the computed tissue viability value.

2. The computer implemented method of claim 1, wherein
the one or more physiological or anatomical parameters
include perfusion territories,
the patient-specific values include a patient tissue perfusion territory estimation,
the method comprises:
estimating a blood supply to the one or more vessel or tissue areas, using a blood flow simulation in at least one of the one or more patient-specific models;
determining the patient tissue perfusion territory estimation based on the estimated blood supply;
modifying the patient-specific model or the patient-specific values of the one or more physiological or anatomical parameters;
determining an effect of the modifying the patient-specific model or at least one of the patient-specific values of the one or more physiological or anatomical parameters on the computed tissue viability value; and
generating a treatment plan based on the determined effect, and
outputting the treatment plan to the electronic storage medium or the display.

3. The computer implemented method of claim 2, wherein the estimated blood supply is for a physiological state that includes a resting patient state, a hyperemic state, an exercise state, a postprandial state, a gravitational state, an emotional state, a state of hypertension, a medicated state, or a combination thereof.

4. The computer implemented method of claim 2, wherein the estimated blood supply includes fractional flow reserve, flow magnitude, flow direction, or a combination thereof.

5. The computer implemented method of claim 2, wherein the treatment plan is generated based further on the modified patient-specific model or the patient-specific values of the one or more physiological or anatomical parameters.

6. The computer implemented method of claim 1, wherein the one or more physiological or anatomical parameters include one or more anatomical characteristics including vessel size, vessel shape, vessel tortuosity, vessel length, vessel thickness, or a combination thereof.

7. The computer implemented method of claim 1, wherein the tissue viability value includes a measure of an extent to which a vessel, tissue, or organ is functional.

8. The computer implemented method of claim 1, wherein:
the computing the tissue viability value further includes inputting, into the machine learning algorithm, one or more image characteristics of the tissue or vessel in one or more physiological states, wherein the one or more image characteristics are derived from the image data and includes, one or more of:
local average intensities,
texture characteristics, and
standard image features.

9. The computer implemented method of claim 1, wherein the computing the tissue viability value further includes inputting, into the machine learning algorithm, one or more secondary characteristics including patient characteristics, target tissue disease characteristics, electromechanical measurements, or a combination thereof.

10. The computer implemented method of claim 1, wherein the computing the tissue viability value further includes comparing blood flow characteristics in the tissue or a vessel at different physiological states.

11. The computer implemented method of claim 1, wherein the one or more patient-specific models include:

a coronary vascular model and a model of the myocardium;
a cerebral vascular model and a model of the brain;
a peripheral vascular model and a model of muscle;
a hepatic vascular model and a model of a liver;
a renal vascular model and a model of a kidney;
a visceral vascular model and a model of a bowel; or
a vascular model representing a vessel and a target organ to which blood is supplied by the vessel.

12. The computer implemented method of claim 1, further comprising:
adjusting the patient-specific values of the one or more physiological or anatomical parameters based on the computed tissue viability value; and
simulating a blood flow characteristic using the computed tissue viability value and the adjusted patient-specific values.

13. A system for estimating patient-specific tissue viability, the system comprising:
a data storage device storing instructions for determining characteristics of tissue viability; and
a processor configured to execute the instructions to perform a method including the steps of:
receiving tissue viability data for a plurality of individuals;
receiving data of one or more physiological or anatomical parameters, for each of the plurality of individuals;
training, by using a training set comprising the tissue viability data and the data of the one or more physiological or anatomical parameters, a machine learning algorithm, wherein the machine learning algorithm maps the one or more physiological or anatomical parameters to tissue viability;
receiving image data derived from one or more images of a patient's anatomy;
generating one or more patient-specific models, each being a model of a vessel or tissue of the patient, using the image data;
calculating patient-specific values of the one or more physiological or anatomical parameters based on the one or more patient-specific models;
computing a tissue viability value by inputting the patient-specific values of the one or more physiological or anatomical parameters into the trained machine learning algorithm, wherein the trained machine learning algorithm includes feature weights defining an extent to which the one or more physiological or anatomical parameters are predictive of tissue viability; and
outputting, to an electronic storage medium or a display, the computed tissue viability value or a treatment plan generated based on the computed tissue viability value.

14. The system of claim 13, wherein
the one or more physiological or anatomical parameters include perfusion territories,
the patient-specific values include a patient tissue perfusion territory estimation,
the method further comprises:
estimating a blood supply to the one or more vessel or tissue areas, using a blood flow simulation in at least one of the one or more patient-specific models;
determining the patient tissue perfusion territory estimation based on the estimated blood supply;
modifying the patient-specific model or the patient-specific values of the one or more physiological or anatomical parameters;
determining an effect of the modifying the patient-specific model or at least one of the patient-specific values of the one or more physiological or anatomical parameters on the computed tissue viability value; and generating a treatment plan based on the determined effect, and outputting the treatment plan to the electronic storage medium or the display.

15. The system of claim 14, wherein the estimated blood supply is for a physiological state that includes a resting patient state, a hyperemic state, an exercise state, a post-prandial state, a gravitational state, an emotional state, a state of hypertension, a medicated state, or a combination thereof.

16. The system of claim 14, wherein the estimated blood supply includes fractional flow reserve, flow magnitude, flow direction, or a combination thereof.

17. The system of claim 13, wherein the tissue viability value includes a measure of the extent to which a vessel, tissue, or organ is functional.

18. The system of claim 13, wherein the estimating the tissue viability value includes comparing blood flow characteristics in a tissue or a vessel at different physiological states.

19. The system of claim 13, wherein the one or more patient-specific models include:
 a coronary vascular model and the myocardium;
 a cerebral vascular model and the brain;
 a peripheral vascular model and muscle;
 a hepatic vascular model and a liver;
 a renal vascular model and a kidney;
 a visceral vascular model and a bowel; or
 a vascular model representing a vessel and a target organ to which blood is supplied by the vessel.

20. A non-transitory computer readable medium for performing a method on a computer system containing computer-executable programming instructions for estimating a characteristic of tissue viability, the method comprising:
 receiving tissue viability data for a plurality of individuals;
 receiving data of one or more physiological or anatomical parameters, for each of the plurality of individuals;
 training, by using a training set comprising the tissue viability data and the data of the one or more physiological or anatomical parameters, a machine learning algorithm, wherein the machine learning algorithm maps the one or more physiological or anatomical parameters to tissue viability;
 receiving image data derived from one or more images of a patient's anatomy;
 generating one or more patient-specific models, each being a model of a vessel or tissue of the patient, using the image data;
 calculating patient-specific values of the one or more physiological or anatomical parameters based on the one or more patient-specific models;
 computing a tissue viability value by inputting the patient-specific values of the one or more physiological or anatomical parameters into the trained machine learning algorithm, wherein the trained machine learning algorithm includes feature weights defining an extent to which the one or more physiological or anatomical parameters are predictive of tissue viability; and
 outputting, to an electronic storage medium or a display, the computed tissue viability value or a treatment plan generated based on the computed tissue viability value.

* * * * *